(12) United States Patent
Frick et al.

(10) Patent No.: US 11,950,363 B2
(45) Date of Patent: Apr. 2, 2024

(54) SENSOR INTERPOSER EMPLOYING CASTELLATED THROUGH-VIAS

(71) Applicant: DexCom, Inc., San Diego, CA (US)

(72) Inventors: Sean Frick, San Francisco, CA (US); Louis Jung, Foster City, CA (US); David Lari, San Francisco, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 17/542,977

(22) Filed: Dec. 6, 2021

(65) Prior Publication Data

US 2022/0095454 A1 Mar. 24, 2022

Related U.S. Application Data

(63) Continuation of application No. 16/850,986, filed on Apr. 16, 2020, now Pat. No. 11,224,125, which is a
(Continued)

(51) Int. Cl.
*H05K 1/09* (2006.01)
*A61B 5/00* (2006.01)
(Continued)

(52) U.S. Cl.
CPC ............ *H05K 1/112* (2013.01); *A61B 5/6802* (2013.01); *H01L 21/768* (2013.01);
(Continued)

(58) Field of Classification Search
CPC . H05K 1/09; H05K 1/11; H05K 1/111; H05K 1/112; H05K 1/114; H05K 1/115;
(Continued)

(56) References Cited

U.S. PATENT DOCUMENTS 4,293,852 A 10/1981 Rogers
4,551,746 A * 11/1985 Gilbert .............. H01L 23/49805
257/691
(Continued)

FOREIGN PATENT DOCUMENTS

JP H11330298 A 11/1999
JP 2006319283 A 11/2006
(Continued)

OTHER PUBLICATIONS

International Search Report and Written Opinion for Application No. PCT/US2019/019103 dated Jul. 17, 2019, 18 pages.
(Continued)

*Primary Examiner* — Xiaoliang Chen
(74) *Attorney, Agent, or Firm* — Snell & Wilmer LLP

(57) ABSTRACT

An example sensor interposer employing castellated through-vias formed in a PCB includes a planar substrate defining a plurality of castellated through-vias; a first electrical contact formed on the planar substrate and electrically coupled to a first castellated through-via; a second electrical contact formed on the planar substrate and electrically coupled to a second castellated through-via, the second castellated through-via electrically isolated from the first castellated through-via; and a guard trace formed on the planar substrate, the guard trace having a first portion formed on a first surface of the planar substrate and electrically coupling a third castellated through-via to a fourth castellated through-via, the guard trace having a second portion formed on a second surface of the planar substrate and electrically coupling the third castellated through-via to the fourth castellated through-via, the guard trace formed between the first and second electrical contacts to provide electrical isolation between the first and second electrical contacts.

19 Claims, 6 Drawing Sheets

Related U.S. Application Data continuation of application No. 16/282,587, filed on Feb. 22, 2019, now Pat. No. 10,660,201.

(60) Provisional application No. 62/634,085, filed on Feb. 22, 2018.

(51) Int. Cl.

| | |
|---|---|
| *A61B 5/1468* | (2006.01) |
| *A61B 5/1495* | (2006.01) |
| *A61B 5/24* | (2021.01) |
| *H01L 21/768* | (2006.01) |
| *H01L 21/78* | (2006.01) |
| *H01L 23/36* | (2006.01) |
| *H01L 23/48* | (2006.01) |
| *H01L 23/50* | (2006.01) |
| *H01L 23/552* | (2006.01) |
| *H05K 1/02* | (2006.01) |
| *H05K 1/11* | (2006.01) |
| *H05K 3/02* | (2006.01) |
| *H05K 3/40* | (2006.01) |
| *A61B 5/145* | (2006.01) |
| *G01N 27/327* | (2006.01) |
| *H05K 1/14* | (2006.01) |

(52) U.S. Cl.
CPC ......... *H01L 23/481* (2013.01); *H05K 1/0262* (2013.01); *H05K 3/403* (2013.01); *A61B 5/14532* (2013.01); *A61B 5/14546* (2013.01); *A61B 5/1468* (2013.01); *A61B 5/6848* (2013.01); *G01N 27/327* (2013.01); *H05K 1/0219* (2013.01); *H05K 1/141* (2013.01); *H05K 2201/0394* (2013.01); *H05K 2201/049* (2013.01); *H05K 2201/0792* (2013.01); *H05K 2201/09063* (2013.01); *H05K 2201/09181* (2013.01); *H05K 2201/10151* (2013.01); *H05K 2201/10378* (2013.01)

(58) Field of Classification Search
CPC ........ H05K 1/118; H05K 1/141; H05K 1/144; H05K 1/181; H05K 1/183; H05K 1/0206; H05K 1/0219; H05K 1/0212; H05K 1/0237; H05K 1/0243; H05K 1/0253; H05K 1/0262; H05K 3/303; H05K 3/361; H05K 3/403; H05K 3/3415; H05K 3/3431; H05K 3/3436; H05K 3/3426; H05K 3/3442; H05K 3/3447; H05K 3/02; H05K 2201/2045; H05K 2201/09181; H05K 2201/10151; H05K 2201/10378; A61B 5/24; A61B 5/0802; A61B 5/1468; A61B 5/1495; A61B 5/14532; A61B 5/14546; A61B 5/6848; H01L 21/78; H01L 21/768561; H01L 21/565; H01L 21/4853; H01L 21/4857; H01L 23/36; H01L 23/48; H01L 23/50; H01L 21/768; H01L 21/561; H01L 23/552
USPC .............. 174/262, 250, 258, 260, 261, 267; 331/69, 70, 100, 107 A, 176; 361/280, 361/743, 763, 767, 811; 257/88, 98, 113, 257/532, 620, 691, 766, 777, 762
See application file for complete search history.

(56) References Cited

U.S. PATENT DOCUMENTS

| | | | | |
|---|---|---|---|---|
| 4,551,747 A | * | 11/1985 | Gilbert | H01L 23/10 257/691 |
| 4,766,368 A | * | 8/1988 | Cox | G01D 5/2417 324/688 |
| 5,369,551 A | * | 11/1994 | Gore | H05K 3/3426 361/767 |
| 5,573,172 A | * | 11/1996 | Gore | H05K 3/3442 228/103 |
| 5,645,709 A | | 7/1997 | Birch et al. | |
| 6,011,693 A | * | 1/2000 | Gore | H05K 3/3426 361/768 |
| 6,144,869 A | | 11/2000 | Berner et al. | |
| 6,554,654 B1 | | 4/2003 | Stoddard et al. | |
| 6,766,149 B1 | * | 7/2004 | Hikita | H03H 9/725 343/702 |
| 7,420,262 B2 | * | 9/2008 | Bauer | H01L 24/94 257/E23.021 |
| 7,830,223 B2 | | 11/2010 | Ahmad | |
| 8,644,029 B1 | * | 2/2014 | Ji | H05K 3/3415 361/811 |
| 9,060,742 B2 | | 6/2015 | Brister et al. | |
| 9,538,636 B1 | | 1/2017 | Weigand et al. | |
| 9,831,414 B2 | * | 11/2017 | Kojo | H03H 9/171 |
| 10,128,592 B1 | * | 11/2018 | Hathaway | H05K 1/115 |
| 10,660,201 B2 | | 5/2020 | Frick et al. | |
| 2001/0032740 A1 | * | 10/2001 | Kennedy | H01L 23/66 174/262 |
| 2002/0020896 A1 | * | 2/2002 | Ishikawa | H05K 3/403 257/E23.061 |
| 2002/0029905 A1 | * | 3/2002 | Okada | H05K 3/403 257/E23.061 |
| 2002/0044022 A1 | * | 4/2002 | Shintani | H03B 5/1203 331/100 |
| 2003/0011075 A1 | * | 1/2003 | Ohuchi | H01L 23/49805 257/E23.105 |
| 2003/0137361 A1 | * | 7/2003 | Knecht | H03L 7/099 331/176 |
| 2006/0000638 A1 | * | 1/2006 | Levine | H01L 23/49805 174/262 |
| 2006/0213685 A1 | * | 9/2006 | Wang | H05K 3/4641 174/262 |
| 2006/0279367 A1 | * | 12/2006 | Knecht | H03B 5/32 331/107 A |
| 2007/0135697 A1 | | 6/2007 | Reggiardo | |
| 2008/0149960 A1 | * | 6/2008 | Amo | H01L 33/505 257/E33.061 |
| 2008/0153451 A1 | * | 6/2008 | Knecht | H04B 1/04 455/349 |
| 2008/0179711 A1 | | 7/2008 | Fujimoto et al. | |
| 2009/0014732 A1 | * | 1/2009 | Nishida | H01L 25/0753 257/E33.072 |
| 2009/0051446 A1 | * | 2/2009 | McCracken | H05K 1/0206 331/69 |
| 2009/0051447 A1 | * | 2/2009 | McCracken | H05K 1/0212 331/70 |
| 2010/0188167 A1 | * | 7/2010 | Devereux | H01P 5/085 333/134 |
| 2013/0078915 A1 | * | 3/2013 | Zhao | H01L 23/48 257/532 |
| 2013/0264910 A1 | * | 10/2013 | Takahashi | H03H 9/15 310/348 |
| 2014/0151105 A1 | * | 6/2014 | Kuwahara | H03H 9/1021 174/250 |
| 2014/0151108 A1 | * | 6/2014 | Mikami | H05K 1/111 174/267 |
| 2015/0145136 A1 | * | 5/2015 | Jensen | H01L 24/64 257/762 |
| 2016/0256070 A1 | | 9/2016 | Murphy et al. | |
| 2017/0188902 A1 | | 7/2017 | Wang et al. | |
| 2017/0188911 A1 | | 7/2017 | Halac et al. | |
| 2017/0307837 A1 | * | 10/2017 | Gektin | G02B 6/4272 |
| 2017/0309558 A1 | * | 10/2017 | Kajihara | H01L 23/49894 |
| 2017/0325332 A1 | * | 11/2017 | Long | H05K 1/144 |
| 2018/0024353 A1 | * | 1/2018 | Tanaka | G02B 26/127 257/113 |
| 2018/0097476 A1 | * | 4/2018 | Aoki | H01L 41/0472 |
| 2018/0211926 A1 | * | 7/2018 | Jang | H01L 23/552 |
| 2019/0117131 A1 | * | 4/2019 | Halac | G16H 40/63 |
| 2019/0261511 A1 | | 8/2019 | Frick et al. | |

(56) References Cited

U.S. PATENT DOCUMENTS

FOREIGN PATENT DOCUMENTS

| WO | WO-2017117469 A1 | 7/2017 |
| WO | WO-2019083939 A1 | 5/2019 |

OTHER PUBLICATIONS

Invitation to Pay Additional Fees and Where Applicable Protest Fee and Partial International Search for Application No. PCT/US2019/019103, mailed May 23, 2019, 13 pages'.
Office Action from European Application No. 19709615.9 dated Sep. 29, 2020, 3 pages.

* cited by examiner

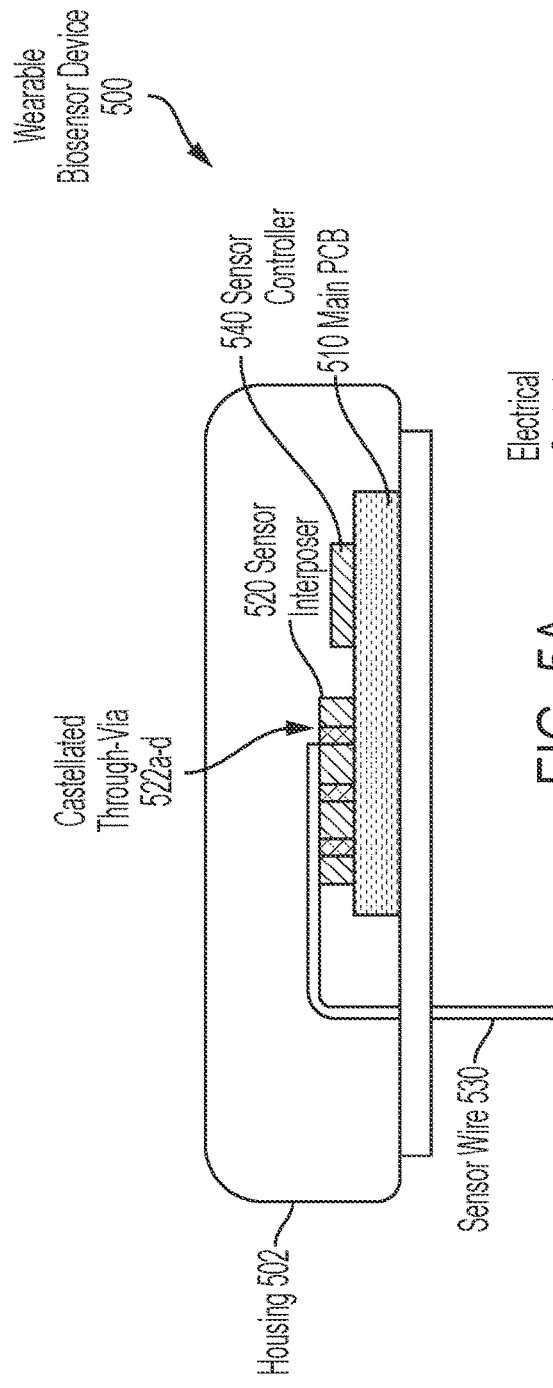
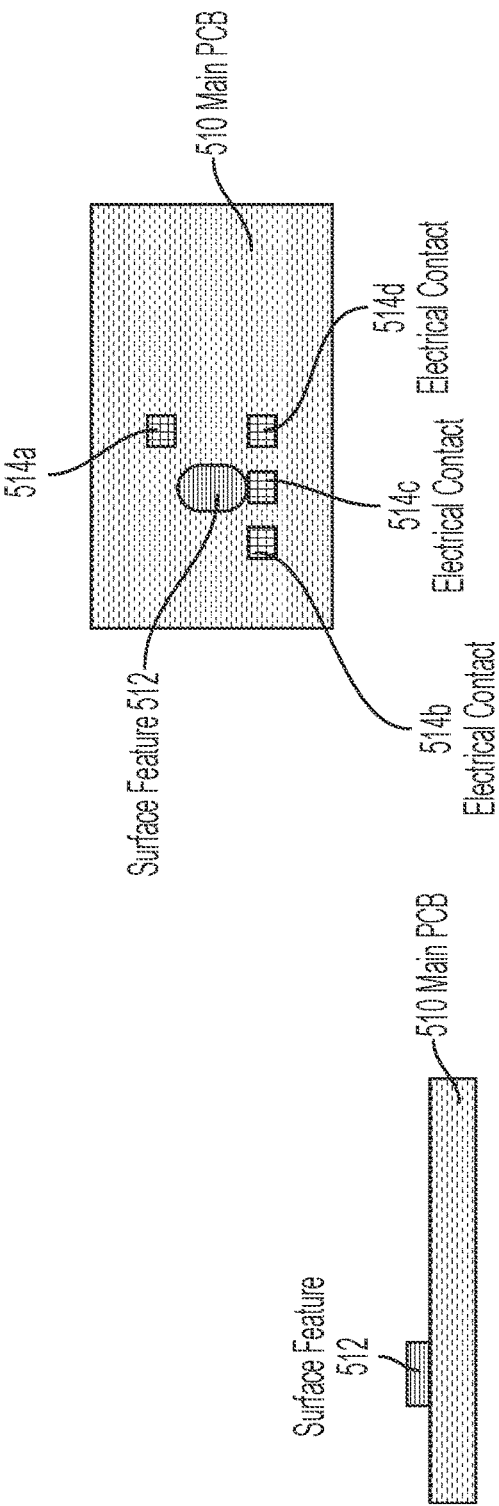

SENSOR INTERPOSER EMPLOYING CASTELLATED THROUGH-VIAS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/850,986, filed Apr. 16, 2020, currently pending, which is a continuation of U.S. application Ser. No. 16/282,587, filed Feb. 22, 2019, now U.S. Pat. No. 10,660,201, issued May 19, 2020, which claims the benefit of U.S. Provisional Application No. 62/634,085, filed on Feb. 22, 2018. Each of the aforementioned applications is incorporated by reference herein in their entireties, and each is hereby expressly made a part of this specification.

FIELD

The present application generally relates to wearable biosensors, and more particularly relates to sensor interposers employing castellated through-vias.

BACKGROUND

Existing wearable biosensors, such as continuous glucose monitors, integrate an analyte sensor into the wearable device as a complete module assembly so that the device may be applied to the body and the sensor wire deployed into the body simultaneously with a single action. As a result, the sensor wire must be electrically connected and mechanically assembled to the device prior to deployment, during device manufacturing or assembly.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 5A-5C shows an example wearable biosensor device including a sensor interposer employing castellated through-vias formed in a PCB.

DETAILED DESCRIPTION

Figure 1:
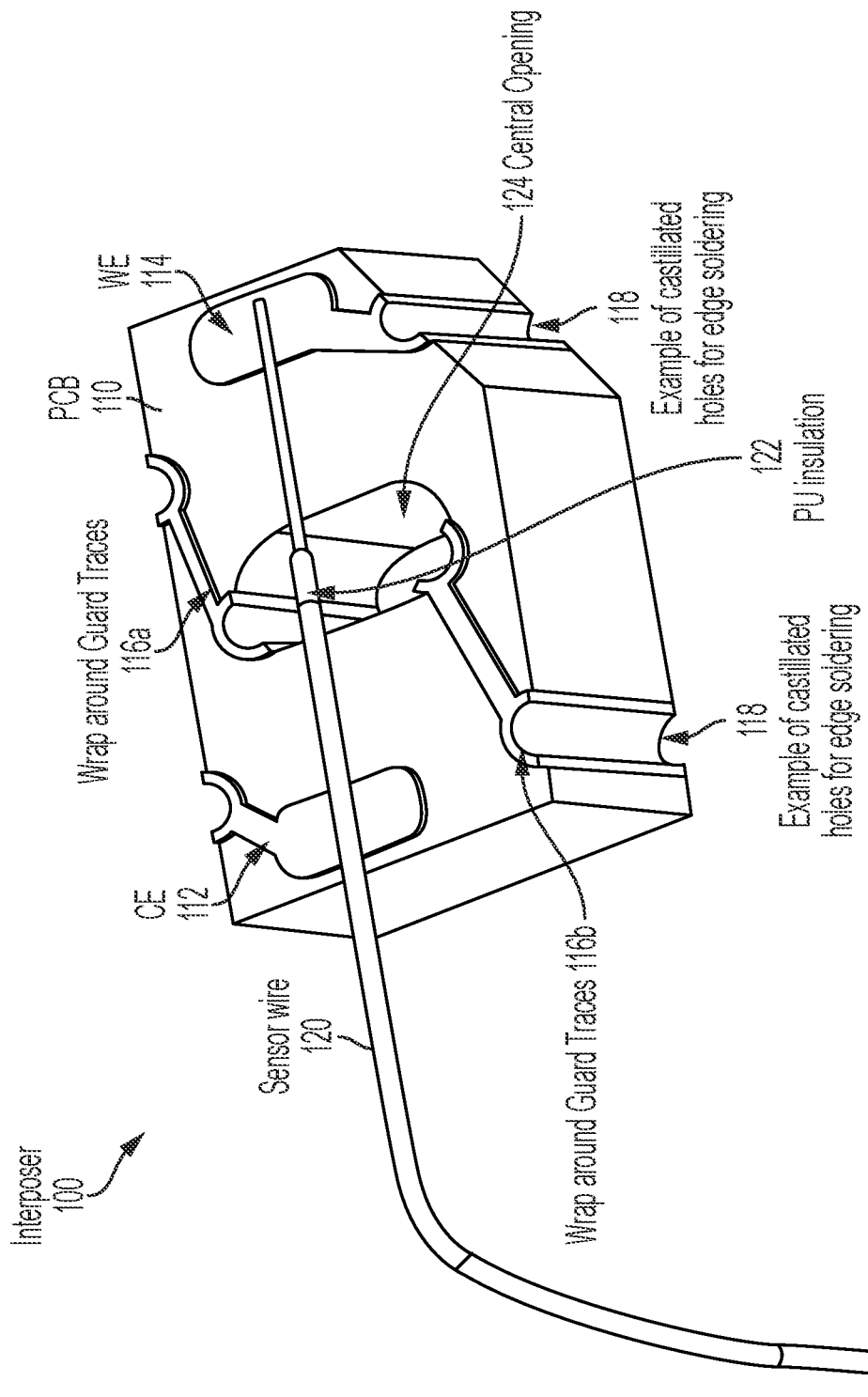
FIGS. 1 and 2 show example sensor interposers employing castellated through-vias formed in a printed circuit board ("PCB")

Examples are described herein in the context of sensor interposers employing castellated through-vias. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Some wearable biosensors employ one or more invasive sensor wires that are inserted into a wearer's skin. The sensor wire typically includes at least two discrete electrodes and has a quantity of a chemical substance, such as glucose oxidase ("GOX"), deposited on the end of the sensor wire that is inserted into the wearer's skin. The chemical then reacts with an analyte present in the wearer's interstitial fluid, which generates a current that can be sensed by the biosensor's electronics. However, because the amount of current generated can be very small, e.g., on the order of tens of nanoamps, and because these chemical substances can be sensitive to heat, the design and manufacture of the biosensor can be difficult. For example, the biosensor must be designed to prevent leakage currents that might interfere with the current generated by the reaction between the chemical substance and the analyte. In addition, manufacturing processes that include high-heat steps, such as soldering, may damage the chemical substance if it is heated.

To address these and other challenges, an example wearable biosensor may employ a main PCB having electronics, such as a microcontroller or wireless transceiver, a battery, etc. In addition, the example device employs a secondary PCB assembly to mechanically secure the sensor wire (generally referred to as an "interposer"), while also providing electrical contacts to different electrodes present on the sensor wire. The interposer can then be electrically and physically coupled to the main PCB, such as by soldering. To help reduce the amount of heat transferred to the interposer during soldering, an example interposer employs castellated through-vias to provide electrical connections between the main PCB and interposer and to provide soldering locations relatively thermally isolated from the sensor wire itself.

In this example, the interposer has through-vias formed around the perimeter of the interposer's footprint. The interposer is then cut from a larger PCB sheet such that the through-vias are cut, exposing the interior portions of the through-vias. The exposed interior portions of the through-vias may be aligned with corresponding electrical contacts on the main PCB and soldered together. Because the solder points are located inside of the through-vias and essentially at the other side of the PCB from the electronics on the interposer PCB, heat transfer from the soldering process to the interposer electronics, including the sensor wire, is substantially reduced. In addition, using through-vias enables one or more guard rings to be formed to encircle the interposer and provide electrical isolation between different electrical contacts formed on the interposer, such as the electrical contacts to different electrodes formed within the sensor wire.

This illustrative example is given to introduce the reader to the general subject matter discussed herein and the disclosure is not limited to this example. The following sections describe various additional non-limiting examples and examples of systems and methods for sensor interposers employing castellated through-vias formed in a PCBs.

Referring now to FIG. 1, FIG. 1 shows an example sensor interposer 100 employing castellated through-vias. In this example, the sensor interposer includes a planar substrate, a PCB in this example. Any suitable PCB material may be employed, including FR4, polyimide, etc. Two electrical contacts 112, 114 are formed on an upper surface of the PCB. Each electrical contact 112, 114 is sized and shaped to enable a sensor wire 120 to be electrically and physically coupled to it, e.g., by clamps, adhesive, or any other suitable physical coupling technique. In this example, the sensor wire is formed from two electrodes formed coaxially, and, prior to use, a sensor chemical (e.g., glucose oxidase) may be deposited on a distal end of the sensor wire, i.e. the end of the sensor wire to be inserted into the wearer's skin. The proximate end of the sensor wire exposes each electrode to enable each electrode to be electrically and physically coupled to a different one of the electrical contacts 112, 114. In this example, the working electrode ("WE") is coupled to electrical contact 114, while the counter electrode ("CE") is coupled to electrical contact 112. In addition, each electrical contact 112, 114 is electrically coupled to a castellated through-via formed on the perimeter edge of the PCB material. Once the interposer 100 is physically and electrically coupled to a main PCB, the castellated through-vias 118 will provide an electrical connection between the electrical contacts 112, 114 and sensor electronics positioned on the main PCB. While in this example, the interposer 100 has two electrical contacts 112, 114, some examples may employ multiple sensor wires, which may require additional electrical contacts based on the type(s) of sensor wire(s) employed. Further, in some examples, the sensor wire may include more than two electrodes. For example, multiple electrodes may be formed on top of each other in successive planar layers. Each layer may be coupled to a different electrical contact formed on the planar substrate. Further, different electrodes may have different sensor chemicals applied to them. Suitable sensor chemicals include chemicals to sense acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, or troponin.

In this example, the planar substrate 110 (or interposer substrate) also defines an opening 124 between the two electrical contacts. The opening provides physical separation between the two electrical contacts 112, 114, thereby providing some electrical isolation between them. In addition, the opening enables the formation of guard traces 116a-b that do not intersect or contact the sensor wire 120. In some examples, the opening may be formed having a shape corresponding to one or more features formed on the main PCB to enable alignment. It should be appreciated, however, that such an opening is not required in all examples, and may be omitted based on design considerations.

In addition to the electrical contacts 112, 114, two guard traces 116a-b have been formed on the interposer PCB. Each guard trace 116a-b encircles a portion of the interposer PCB to provide electrical isolation between the two electrical contacts 112, 114. In this example, each guard ring includes a portion formed on the upper surface of the interposer PCB 110 that electrically couples two corresponding castellated through-vias. Each guard ring 116a-b also includes a portion formed on the lower surface of the interposer PCB 110 that is also coupled to the same corresponding castellated through-vias to provide a closed loop of material encircling a portion of the interposer PCB. In combination with the opening, the two guard rings 116a-b electrically isolate the two electrical contacts 112, 114 from each other. In some examples, one or both of the guard rings 116a-b may be coupled to a ground plane to help dissipate leakage current.

In this example, the interposer 100 also includes a sensor wire 120 that is coupled to the two electrical contacts 112, 114. The sensor wire 120 in this example has two wire materials arranged coaxially, one of which operates as a working electrode and the other operates as a reference electrode or a counter electrode. To enable the two different coaxial portions of the sensor wire to couple to different electrical contacts, the interior wire material extends beyond the end of the exterior wire material, though a portion of it is covered by a polyurethane insulation 122. In this example, the interior wire material is physically and electrically coupled to one electrical contact 114 and the exterior wire material is physically and electrically coupled to the other electrical contact 112.

In this example, the sensor wire materials are (1) a platinum or platinum-coated wire, which is the interior wire material, and (2) a silver/silver-chloride (Ag/AgCl) material that is the exterior wire material. One end of the sensor wire 120 and a portion of the Ag/AgCl material are inserted into the patient's skin, while the other end of the sensor wire 120 is attached to the electrical contacts. The Ag/AgCl material is coupled to the first electrical contact 112, while the platinum material is coupled to the second electrical contact 114.

Figure 2:
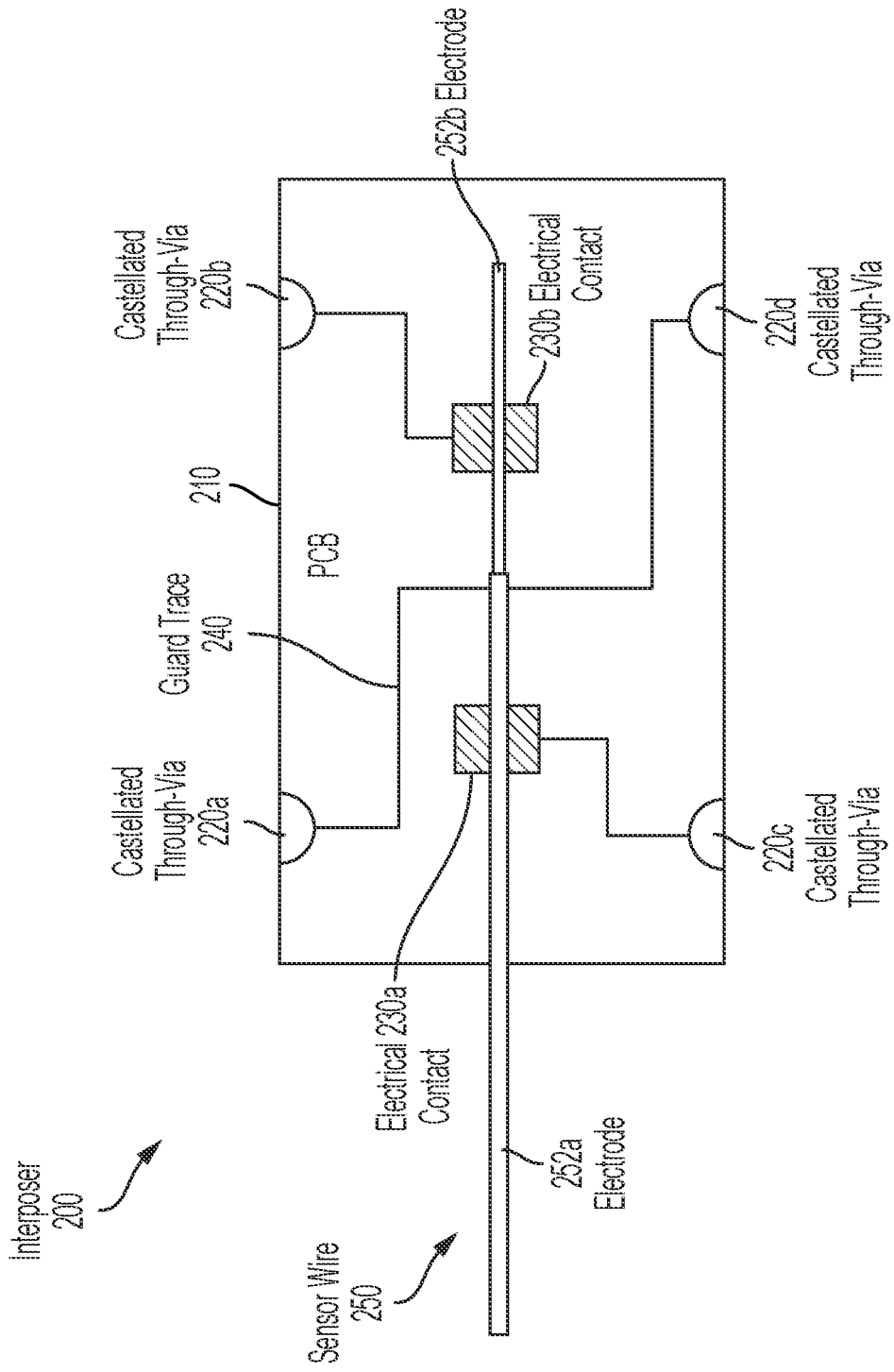

Referring now to FIG. 2, FIG. 2 illustrates another example sensor interposer 200 employing castellated through-vias. In this example, the interposer 200 is formed from a planar substrate, which is a PCB 210. Similar to the example shown in FIG. 1, the interposer 200 has two electrical contacts 230a-b formed on it. A sensor wire 250 is physically and electrically coupled to the electrical contacts 230a-b. In particular, the sensor wires has two coaxial electrodes 252a-b, which are physically and electrically coupled to the respective electrical contacts 230a-b. Each electrical contact 230a-b is electrically coupled to a corresponding castellated through-via 220b, 220c by an electrical trace formed on the PCB 210. The castellated through-vias may later be physically and electrically coupled to electrical contacts on another PCB to allow electrical signals from the sensor wire 250 to be communicated to the other PCB.

The interposer 200 also includes a guard trace 240 formed on the PCB 210. The guard trace 240 traverses the PCB 210 between two castellated through-vias 220a, 220d and between the two electrical contacts 230a-b, thereby electrically isolating them from each other. In this example, the guard trace 240 is formed both on the upper surface of the PCB (shown in FIG. 2) as well as on the lower surface, opposite the upper surface, where a further electrical trace is formed between the castellated through-vias 220a, 220d. However, in some examples, the guard trace 240 may only be formed on the same surface as the electrical contacts 230a-b. In this example, unlike the example shown in FIG. 1, the PCB does not define a central opening. Thus, the guard trace 240 must run beneath the sensor wire 250 without contacting the sensor wire 250, which may disrupt electrical signals provided by the sensor wire 250 to the electrical contacts 230a-b.

Figure 3A:
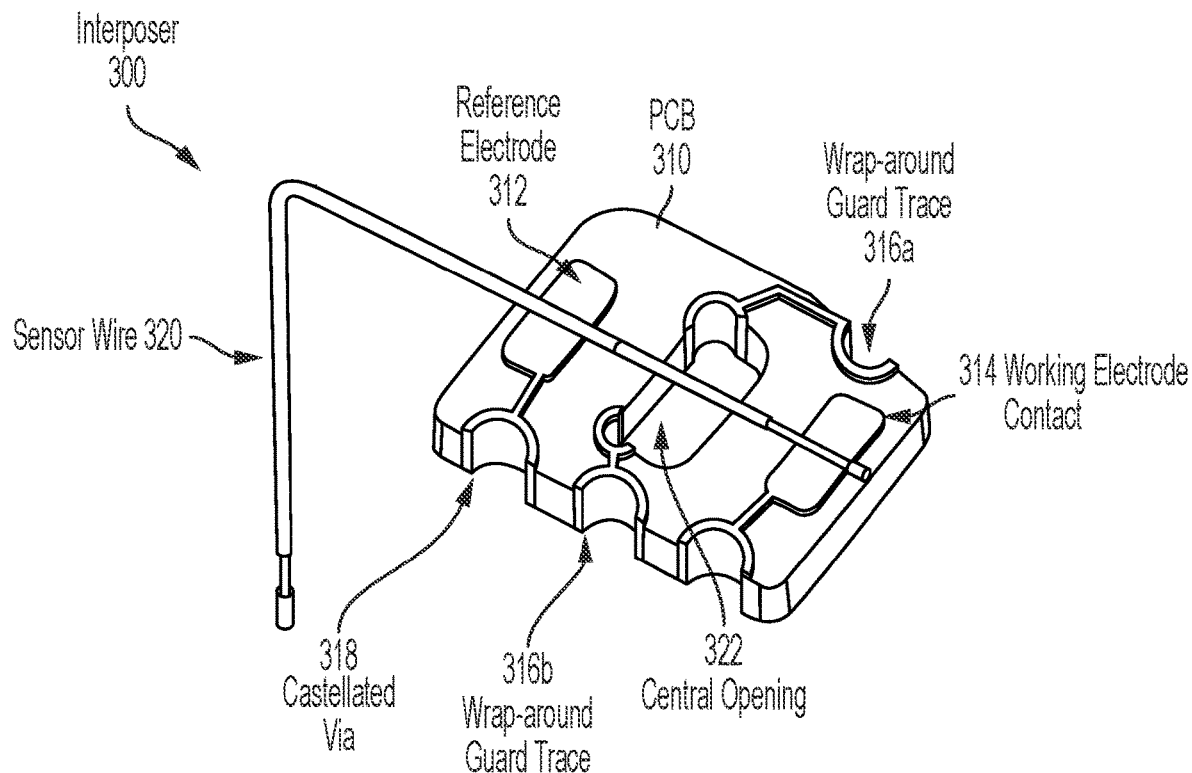
FIGS. 3A-3B show an example sensor interposer employing castellated through-vias formed in a PCB.
Figure 3B:
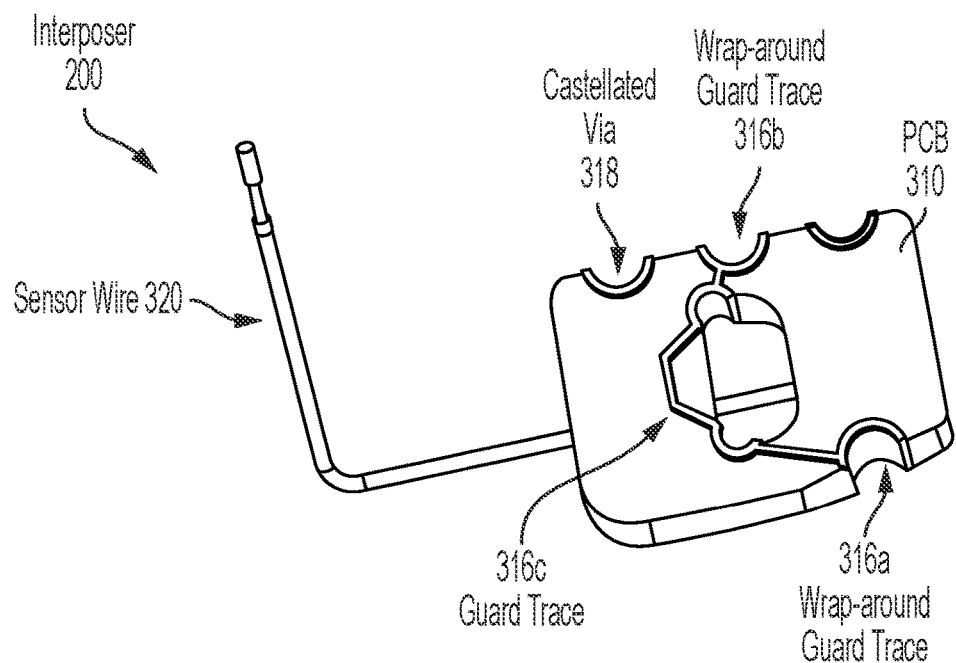

Referring now to FIGS. 3A-3B, FIG. 4A shows an example sensor interposer 300 employing castellated through-vias formed in a PCB. In this example, the interposer 300 has a PCB 310 planar substrate that defines a central opening 322. In addition, the PCB 310 has four castellated through-vias formed on its perimeter, while two castellated through-vias are formed on the perimeter of the central opening 322.

Two electrical contacts 312, 314 are formed on the upper surface of the PCB and are each electrically coupled to a corresponding castellated through-via formed on the perimeter of the central opening 322. The electrical contacts 312, 314 are arranged to physically and electrical couple to a sensor wire 220.

In addition to the electrical contacts 312, 314, two "wrap-around" guard traces 316a-b are formed on the PCB 310. Each guard trace 316a-b encircles a portion of the PCB 310 to provide electrical isolation between the two electrical contacts 312, 314. In this example, each guard trace 316a-b includes a portion formed on the upper surface of the PCB 310 that electrically couples two corresponding castellated through-vias. Each guard trace 316a-b also includes a portion formed on the lower surface of the PCB 310 that is also coupled to the same corresponding castellated through-vias to provide a closed loop of material encircling a portion of the PCB 310. In combination with the opening, the two guard traces 316a-b electrically isolate the two electrical contacts 312, 314 from each other. In some examples, one or both of the guard traces 316a-b may be coupled to a ground plane to help dissipate leakage current.

FIG. 3B shows a lower surface of the PCB 310. The view shown in FIG. 4B also illustrates the wrap-around guard traces 316a-b, which are electrically coupled by a guard trace 316c that couples the two castellated through-vias formed in the perimeter of the opening. In some examples, guard trace 316c is not included, thus the two wrap-around guard traces 316a-b are electrically isolated from each other on the PCB 310, though in some examples, they may be coupled to a common ground plane, such a common ground plane formed on a main PCB of a biosensor.

Figure 4:
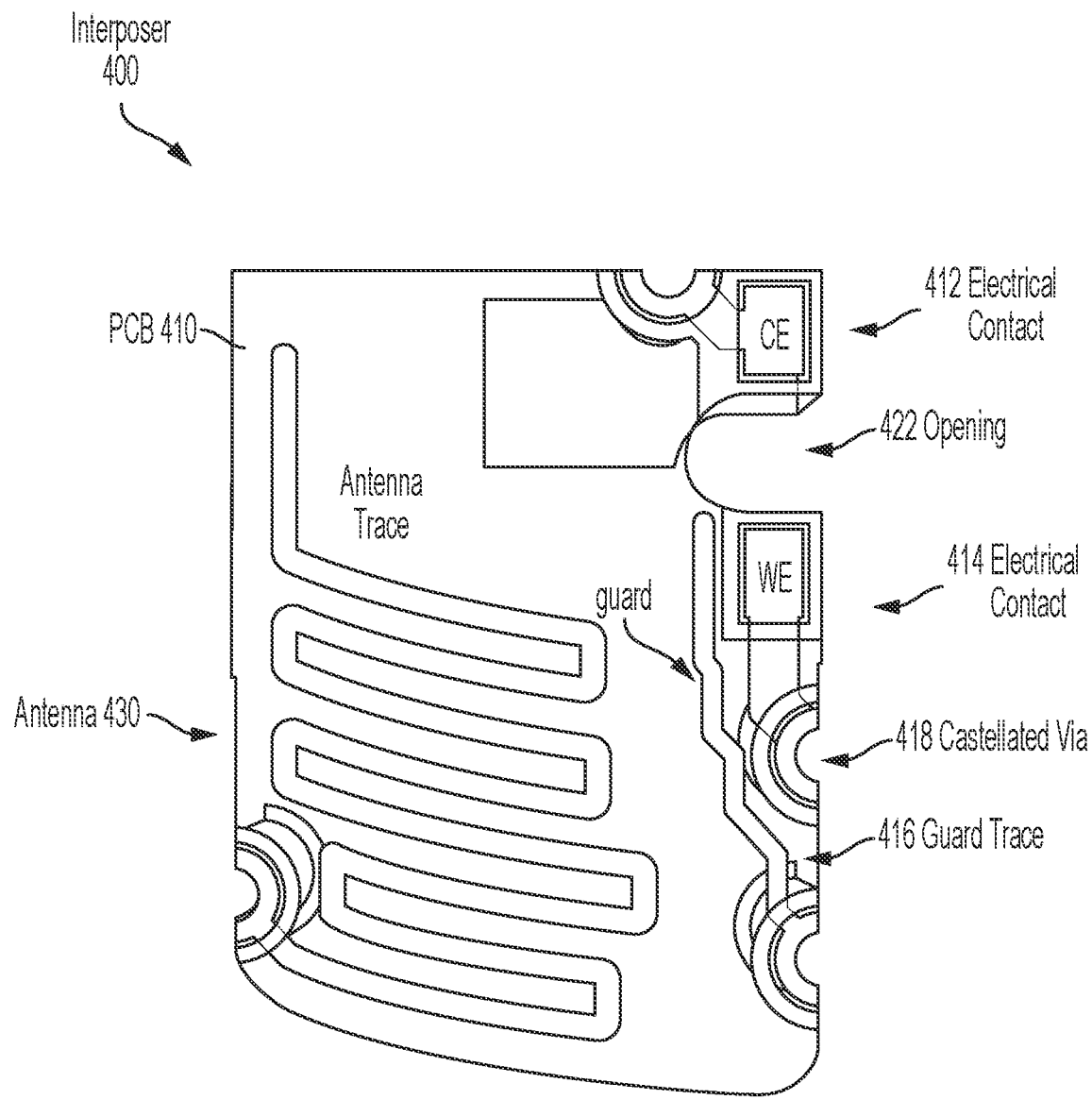
FIG. 4 shows an example sensor interposer employing castellated through-vias formed in a PCB.

Referring now to FIG. 4, FIG. 4 shows an example sensor interposer 400 employing castellated through-vias formed in a PCB. Such an example sensor interposer 400 may be integrated within a wearable biosensor, such as a continuous glucose monitor ("CGM"). An example CGM may include a main PCB that includes various electronic components, including a processor, discrete electronic components, and a wireless transceiver. A battery may be mounted on and electrically coupled to the CGM's main PCB to supply power to the electronic components of the CGM.

The example sensor interposer 400 may be physically and electrically coupled to the main PCB to enable signals from the CGM's sensor wire, physically and electrically coupled to the sensor interposer 400, to be provided to electronic components on the main PCB, such as the processor.

The sensor interposer 400 in this example includes two electrical contacts 412, 414 formed on one side of the interposer 400, which are physically separated by an opening 422 defined in the perimeter of the interposer 400. Each electrical contact 412, 414 is electrically coupled to a castellated through-via. In addition, a guard trace 416 is formed on the same surface of the PCB 410 as the two electrical contacts 412, 414 and provides electrical isolation between the two electrical contacts 412, 414.

In addition to the electrical contacts and guard trace 416, the interposer 400 also includes additional electrical features. In this example, an electrical tracer designed as an antenna 430 is formed on the PCB 410, and electrically coupled to a castellated through-via to enable electrical and physical coupling to the CGM's main PCB. In some examples, still other electrical features may be provided on the PCB, including additional electrical contacts to physically and electrically couple one or more additional sensor wires.

In some examples, the interposer 400 may be formed separately from the main PCB, and the sensor wire may be physically and electrically coupled to the interposer 400 before the interposer 400 is physically and electrically coupled to the CGM's main PCB; however, as will be discussed with respect to FIG. 6, other sequences may be employed as well.

Referring now to FIGS. 5A-5C, FIG. 5A shows an example wearable biosensor device 500 that includes a sensor interposer 520 employing castellated through-vias. In this example, the wearable biosensor device 500 includes a main PCB 510 on which are positioned a sensor interposer 520 and a sensor controller 540. This example device 500 includes the example sensor interposer shown in FIG. 3; however, any suitable sensor interposer employing castellated through-vias may be employed.

In this example, the main PCB 510 also defines a surface feature 512, such as a pin that engages with an opening defined in the sensor interposer 520. FIG. 5B illustrates the main PCB 510, which has a surface feature 512 defined on it. The surface feature 512 provides an alignment feature to enable alignment of the sensor interposer 520 with the main PCB 510 and one or more electrical contacts formed on the main PCB 510. FIG. 5C illustrates a top-down view of the main PCB 510, which has the surface feature 512 formed and positioned to engage with a sensor interposer 520. In addition, the main PCB 510 has four electrical contacts 514a-d formed to engage with the sensor interposer's castellated through-vias 522a-d.

Figure 6:
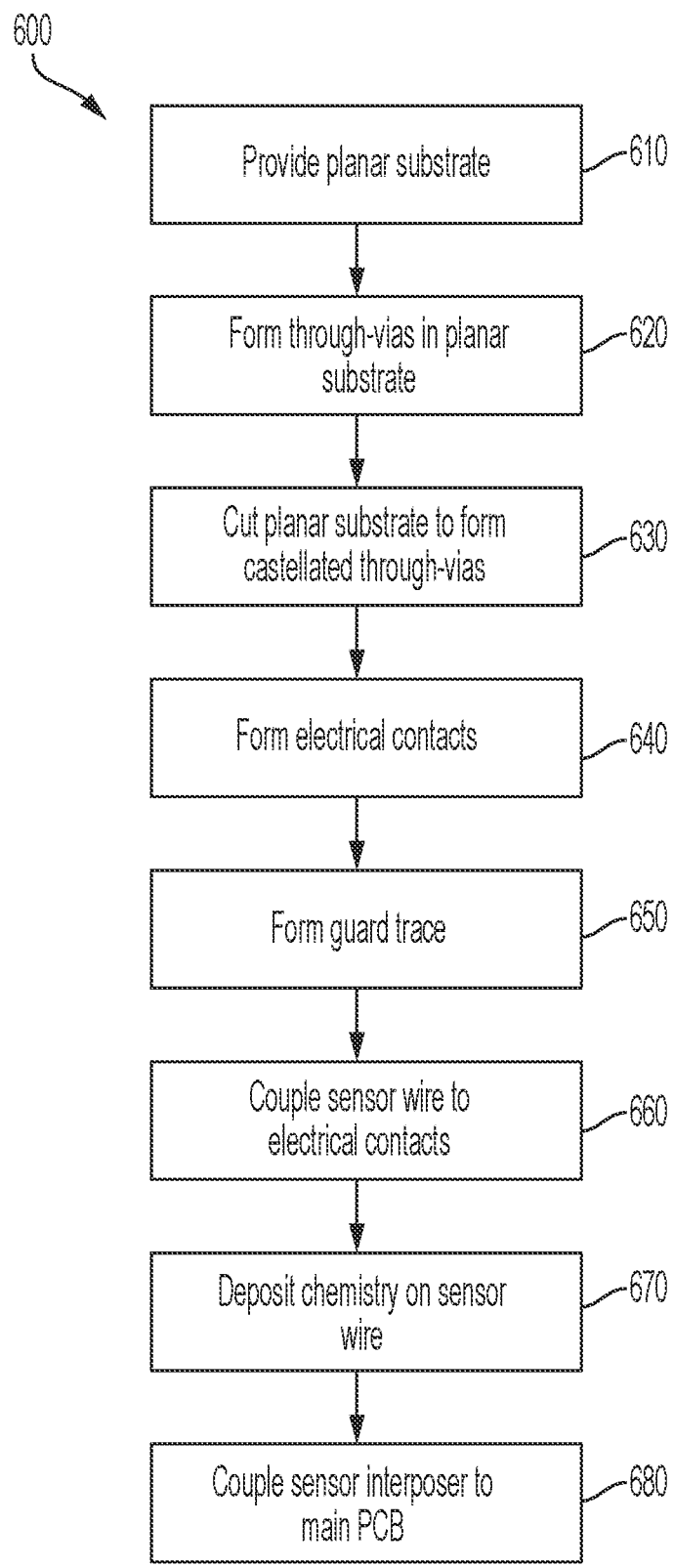
FIG. 6 shows an example method of manufacturing a sensor interposer employing castellated through-vias formed in a PCB.

Referring now to FIG. 6, FIG. 6 shows an example method 600 for manufacturing a sensor interposer employing castellated through-vias formed in a PCB. The example method 600 will be described with respect to the example sensor interposer 100 shown in FIG. 1; however, example methods according to this disclosure may be employed to manufacture any suitable example sensor interposer according to this disclosure.

At block 610, a suitable planar substrate 110 is provided. In this example, the planar substrate 110 is a PCB formed of a suitable material, such as FR4 or polyimide. The planar substrate 110 in this example has a larger size than the designed sensor interposer 100. Thus, at a later step, the planar substrate 110 may be cut to the designed size for the sensor interposer 100.

At block 620, one or more through-vias 118 are formed in the planar substrate 110, such as in locations corresponding to a designed perimeter of a sensor interposer 100. Such through-vias 118 may be formed having substantially circular (or other) cross-sections, where a portion of the through-via's perimeter extends outside of the designed perimeter of the sensor interposer 100. In some examples, one or more through-vias 118 may be formed in an interior portion of the sensor interposer 100 as well. Such through-vias 118 may be formed around a designed perimeter of an opening to be defined in the sensor interposer 100. For example, referring again to FIG. 1, two through-vias were formed in the PCB 110 and were cut to form castellated through-vias when the central opening in the PCB 110 was formed. Any suitable number of through-vias may be formed according to different examples. In this example, four through-vias are formed on the designed perimeter of the sensor interposer, while two additional through-vias are formed on the designed perimeter of a central opening of the sensor interposer 100.

At block 630, the planar substrate 110 is cut along a designed perimeter of the sensor interposer 100, including cutting the through-vias to form castellated through-vias 118. In this example, the planar substrate 110 is further cut to form the central opening 124 and the castellated through-vias in the perimeter of the central opening 124.

At block 640, two electrical contacts 112, 114 are formed on the PCB 110 within the designed perimeter of the sensor interposer 100. In this example, the electrical contacts 112, 114 are formed to enable physical and electrical coupling of a sensor wire 120 and are formed on opposite sides of a designed central opening 124. In this example, both electrical contacts 112, 114 are formed on the same surface of the PCB 110; however, in some examples, they may be formed on opposite sides of the PCB 100. For example, if each electrode of a sensor wire is formed into a discrete wire, they may be coupled to opposite sides of the PCB 110. And while in this example, two electrical contacts are formed, in some examples, more than two electrical contacts may be formed. For example, if multiple sensor wires are to be affixed to the sensor interposer, a pair of electrical contacts may be formed for each sensor wire or sensor electrode.

In addition to forming the electrical contacts at block 640, an electrical trace from each electrical contact 112, 114 is formed to electrically couple the respective electrical contact 112, 114 to a corresponding castellated through-via. In some examples, the electrical traces may be serpentine to extend their length to reduce heat transfer from the castellated via to the electrical contact when the interposer is later soldered to the main PCB.

At block 650, one or more guard traces 116a-b are formed on the PCB 110. In this example, electrical traces are formed to couple castellated through-vias to each other to electrically isolate the electrical contacts. For example, referring to FIG. 3A, electrical traces are formed between the castellated through-vias formed in the perimeter of the central opening 322 and a corresponding castellated through-via formed in the perimeter of the PCB 310. Such traces are formed on both the upper and lower surfaces of the PCB 310 to create guard traces that encircles the PCB 210. In addition, in this example, a guard trace 316c is formed between the castellated though-vias formed in the perimeter of the central opening 322 to couple the two wrap-around guard traces 316a-b; however guard trace 316c is optional and may be omitted in some examples.

At block 660, a sensor wire 120 is coupled to the electrical contacts 112, 114. As discussed above, a sensor wire 120 may be a coaxial sensor wire 120 having two different wire materials with the inner wire material extending beyond the outer wire material at one end of the sensor wire 120. A portion of the exposed inner wire material may be physically and electrically coupled to one of the electrical contacts 114, such as by soldering or using a clip or other electrical coupling means. A portion of the outer wire material may be coupled to the other electrical contact 112 using any suitable electrical coupling means.

At block 670, suitable sensor chemistry, such as glucose oxidase, is deposited on the end of the sensor wire 120 distal from the sensor interposer 100.

At block 680, the sensor interposer 100 is coupled to a biosensor's main PCB. In this example, the sensor interposer 100 is soldered to the main PCB using each of the castellated through-vias formed in the perimeter of the sensor interposer. In some examples, the castellated through-vias formed in the perimeter of the central opening may be soldered instead or in addition.

While the steps of the method 600 above were described in a particular order, it should be appreciated that different orders may be employed according to different examples. For example block 630 maybe performed after block 650, or block 650 may be performed before block 640 or block 630.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A sensor interposer comprising:
   a planar substrate defining a plurality of castellated through-vias;
   a first electrical contact formed on the planar substrate and electrically coupled to a first castellated through-via;
   a second electrical contact formed on the planar substrate and electrically coupled to a second castellated through-via, the second castellated through-via electrically isolated from the first castellated through-via, wherein the planar substrate defines a closed perimeter through hole between the first and second electrical contacts;
   a first guard trace formed on the planar substrate, the first guard trace electrically coupled between a third and a fourth castellated through-via, the first guard trace isolating the first and second electrical contacts, wherein the third castellated through-via is formed in a perimeter of the planar substrate, and the fourth castellated through-via is formed in a perimeter of the closed perimeter through hole, and;
   a second guard trace formed on the planar substrate, the second guard trace electrically coupled between a fifth and a sixth castellated through-via, the second guard trace isolating the first and second electrical contacts, wherein the fifth castellated through-via is formed in the perimeter of the planar substrate, and the sixth castellated through-via is formed in the perimeter of the closed perimeter through hole.

2. The sensor interposer of claim 1, wherein the first guard trace comprises
   a first portion formed on a first surface of the interposer substrate and electrically coupling the third castellated through-via to the fourth castellated through-via, and a second portion formed on a second surface of the interposer substrate and electrically coupling the third castellated through-via to the fourth castellated through-via, the first guard trace formed between the first and second electrical contacts to provide electrical isolation between the first and second electrical contacts.

3. The sensor interposer of claim 1, wherein the second guard trace comprises a first portion formed on a first surface of the planar substrate and electrically coupling the fifth castellated through-via to the sixth castellated through-via, and a second portion formed on a second surface of the planar substrate and electrically coupling the fifth castellated through-via to the sixth castellated through-via, the second guard trace formed between the first and second electrical contacts to provide electrical isolation between the first and second electrical contacts.

4. The sensor interposer of claim 1, further comprising a sensor wire electrically coupled to the first and second electrical contacts.

5. The sensor interposer of claim 4, wherein the sensor wire comprises a first wire material and a second wire material, the second wire material formed coaxially around the first wire material, a first portion of the first wire material extending beyond the second wire material at a first end of the sensor wire, wherein the first portion of the first wire material is electrically coupled to the first electrical contact, and the second wire material is coupled to the second electrical contact.

6. The sensor interposer of claim 5, wherein the first wire material comprises a platinum wire or a platinum-coated wire, and the second wire material comprises silver or silver-chloride.

7. The sensor interposer of claim 4, wherein the sensor wire is physically coupled to the first and second electrical contacts by clamps or adhesive.

8. The sensor interposer of claim 4, wherein a proximate end of the sensor wire exposes a first and second electrode to enable the electrical coupling to the first and second electrical contacts.

9. The sensor interposer of claim 4, wherein a distal end of the sensor wire is configured to be inserted into a wearer's skin.

10. The sensor interposer of claim 4, wherein a sensor chemical is disposed on a distal end of the sensor wire.

11. The sensor interposer of claim 10, wherein the sensor chemical comprises glucose oxidase.

12. The sensor interposer of claim 10, wherein the sensor chemical comprises a chemical configured to react with one or more of glucose, lactate, or cholesterol.

13. The sensor interposer of claim 10, wherein the sensor chemical comprises a chemical configured to sense one or more of acetyl choline, amylase, bilirubin, chorionic gonadotropin, creatine kinase, creatine, DNA, fructosamine, glutamine, growth hormones, hormones, ketones, peroxide, prostate-specific antigen, prothrombin, RNA, thyroid stimulating hormone, or troponin.

14. The sensor interposer of claim 1, wherein the planar substrate is formed of FR4 or a polyimide material.

15. The sensor interposer of claim 1, wherein the first electrical contact and the second electrical contact are formed on opposite sides of the planar substrate.

16. The sensor interposer of claim 1, wherein the first guard trace is coupled to a ground plane configured to dissipate leakage current.

17. The sensor interposer of claim 1, wherein an opening in the planar substrate is configured to engage with a surface feature of a main printed circuit board and configured to align the sensor interposer with the main printed circuit board.

18. The sensor interposer of claim 1, further comprising an antenna.

19. The sensor interposer of claim 18, wherein the antenna is formed as an electrical tracer on the planar substrate and is configured to electrically couple with an electrical contact on a main printed circuit board.

* * * * *